United States Patent
Reed et al.

(10) Patent No.: US 6,770,675 B2
(45) Date of Patent: Aug. 3, 2004

(54) COMPOSITIONS AND METHODS FOR REDUCING OCULAR HYPERTENSION

(75) Inventors: Kenneth Warren Reed, Lawrenceville, GA (US); Shau Fong Yen, Atlanta, GA (US); Mary Sou, Alpharetta, GA (US); Regina Flinn Peacock, Alpharetta, GA (US)

(73) Assignee: Novartis AG, Bern (CH)

( * ) Notice: Subject to any disclaimer, the term of this patent is extended or adjusted under 35 U.S.C. 154(b) by 252 days.

(21) Appl. No.: 09/812,162

(22) Filed: Mar. 19, 2001

(65) Prior Publication Data

US 2002/0002185 A1 Jan. 3, 2002

Related U.S. Application Data

(63) Continuation-in-part of application No. 09/042,817, filed on Mar. 17, 1998, now abandoned.
(60) Provisional application No. 60/093,065, filed on Mar. 17, 1997.

(51) Int. Cl.$^7$ ............................................. A61K 31/215
(52) U.S. Cl. ...................... 514/530; 514/573; 514/912; 514/913
(58) Field of Search ................................. 514/530, 575, 514/912, 913

(56) References Cited

U.S. PATENT DOCUMENTS

| | | | |
|---|---|---|---|
| 5,001,153 A | 3/1991 | Ueno et al. | 514/530 |
| 5,057,621 A | * 10/1991 | Cooper et al. | 560/53 |
| 5,106,869 A | 4/1992 | Ueno et al. | 514/530 |
| 5,151,444 A | 9/1992 | Ueno et al. | 514/530 |
| 5,166,178 A | 11/1992 | Ueno et al. | 514/573 |
| 5,208,256 A | 5/1993 | Ueno | 514/530 |
| 5,212,200 A | 5/1993 | Ueno et al. | 514/530 |
| 5,221,763 A | 6/1993 | Ueno et al. | 560/121 |
| 5,236,907 A | 8/1993 | Ueno et al. | 514/530 |
| 5,238,961 A | 8/1993 | Woodward et al. | 514/573 |
| 5,296,504 A | 3/1994 | Stjernschantz et al. | 514/530 |
| 5,422,368 A | 6/1995 | Stjernschantz et al. | 514/530 |
| 5,446,041 A | 8/1995 | Chan et al. | 514/530 |
| 5,558,876 A | 9/1996 | Desai et al. | 424/427 |
| 5,578,618 A | 11/1996 | Stjernschantz et al. | 514/365 |

FOREIGN PATENT DOCUMENTS

| | | |
|---|---|---|
| EP | 0 458 587 A1 | 5/1991 |
| JP | 07316060 | 2/1996 |
| WO | WO 9213836 | 2/1992 |
| WO | WO 9530420 | 5/1995 |

* cited by examiner

*Primary Examiner*—Zohreh Fay
(74) *Attorney, Agent, or Firm*—David E. Wildman

(57) ABSTRACT

An improved ophthalmic composition, including docosanoid active agents, which is especially useful in lowering intraocular pressure associated with glaucoma. Improvements in IOP reduction efficacy, preservative efficacy and reduced additive concentrations are achieved by utilizing the disclosed compositions which include a docosanoid active agent (e.g., isopropyl unoprostone), in conjunction with selected non-ionic surfactants, preservatives, and non-ionic tonicity adjusting agents.

9 Claims, 1 Drawing Sheet

COMPOSITIONS AND METHODS FOR REDUCING OCULAR HYPERTENSION

This application is a continuation-in-part of U.S. patent application Ser. No. 09/042,817, filed Mar. 17, 1998, abandoned, which claimed priority under 35 U.S.C. §119(e) from U.S. Provisional Patent application Serial No. 60/093,065, abandoned, which was converted from U.S. patent application Ser. No. 08/819,221, filed Mar. 17, 1997, abandoned.

FIELD OF THE INVENTION

The invention relates broadly to ophthalmic technology. More specifically, this invention relates to the therapeutic treatment of the eye to reduce elevated intraocular pressure, for example, the elevated intraocular pressure which is associated with glaucoma.

BACKGROUND OF THE INVENTION

U.S. Pat. No. 5,208,256 teaches a method of treating ocular hyertension by ocularly administering a combination of a docosanoid compound, e.g., [1R-[1α(Z),2β,3α,5α]]-7-[3,5-Dihydroxy-2-(3-oxodecyl)cyclopentenyl]-5-heptenoic acid or a salt or ester thereof and a polyoxyethylenesorbitan unsaturated higher aliphatic acid monoester. Preferred examples of the latter includes myristoleic acid, palmitoleic acid, oleic acid, gadoleic acid and linoleic acid. Polyoxyethylene (20) sorbitan monooleate is also known as Polysorbate 80 and sold, inter alia, under the names SORLATE, CRILLET, TWEEN 80, MONITAN and OLOTHORB.

CREMOPHOR has been used as a surfactant in eye drops (See Japanese Patent 07316060, filed on Dec. 16, 1994). CREMOPHOR is an ethoxylated, hydrogenated castor oil, which is also referred to as a polyoxyethylene hardened castor oil. However, the use of CREMOPHOR with docosanoids in an ophthamic delivery system has not been disclosed or suggested.

While docosanoids are useful for reducing intraocular pressure, there is a need to improve the efficacy of medicaments containing them. In addition, there is a need for improvement in the preservative effectiveness of ophthalmic docosanoid compositions which include surfactants, while maintaining good efficacy and good ocular tolerance. Furthermore, improvements in the shelf life of ophthalmic docosanoid compositions are desirable. Also, it is always desirable to reduce manufacturing difficulties. Thus, there is a need for a docosanoid-containing ophthalmic composition that can be manufactured with a minimum of complexity and which exhibits a balance of efficacy, preservative effectiveness, ocular tolerance, and a long shelf life.

SUMMARY OF THE INVENTION

An object of the invention is to improve the efficacy of docosanoid-containing ophthalmic compositions.

Another object of the invention is to improve the preservative effectiveness of docosanoid-containing ophthalmic compositions.

Still another object of the invention is to improve shelf life of docosanoid-containing ophthalmic compositions.

Yet another object of the invention is to reduce the complexity of manufacturing a docosanoid-containing ophthalmic composition.

A further object of the invention is to produce a docosanoid-containing ophthalmic composition with a desirable balance of efficacy, preservative effectiveness, ocular tolerance, and shelf life.

These and other objects and advantages of the invention are achieved with the various embodiments of the present docosanoid-containing ophthalmic compositions, methods of use and methods of manufacture. One embodiment of the invention is an ophthalmic composition which includes a docosanoid, a non-ionic surfactant (e.g. a CREMOPHOR) and a preservative (e.g. benzalkonium chloride). Another embodiment is an ophthalmic composition which includes a docosanoid, a surfactant, a non-ionic tonicity adjusting agent (e.g. mannitol) and a preservative. Still another embodiment is an ophthalmic composition which includes a docosanoid, one or more surfactants, a strong preservative (e.g. BAK) and a preservative enhancer (e.g., EDTA). Yet another embodiment of the invention relates to adding a buffer to improve product shelf life and reduce production complexity.

DETAILED DESCRIPTION OF THE INVENTION

Figure 1:
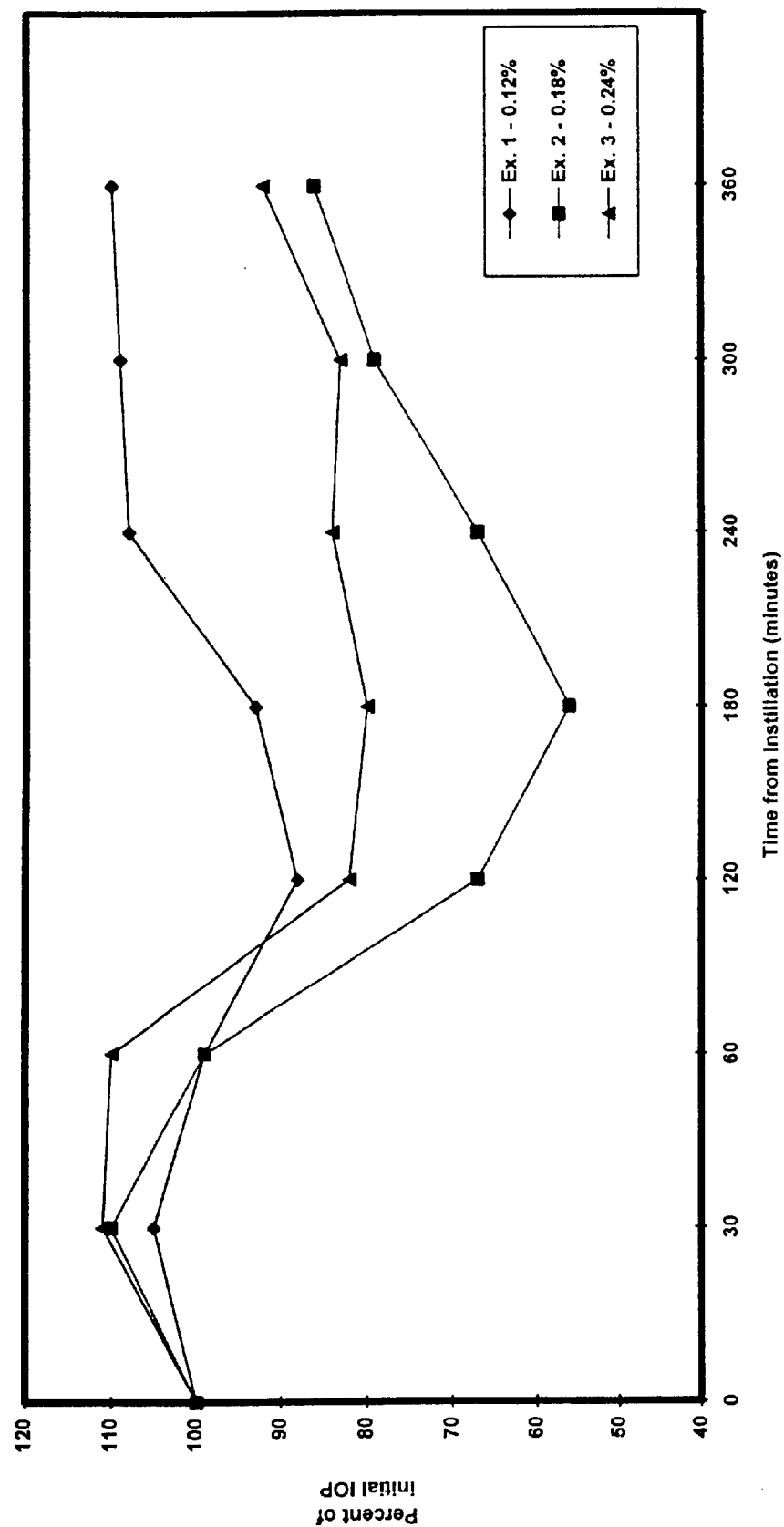
FIG. 1 is a graph showing the time-course changes in the intraocular pressure of a rabbit eye, which received instillation of a 0.12%, 0.18% or 0.24% isaprapyl unaprostone ophthalmic formulation.

The various embodiments of the invention offer a number of improvements in docosanoid compositions which are useful, inter alia, for reducing intraocular pressure. The compositions are especially useful in treating elevated intraocular pressure associated with glaucoma. Accordingly, all of the components of the compositions are preferably ophthalmically acceptable, at the concentrations of use and under the conditions in which they are applied. An "ophthalmically acceptable" component, as used herein, refers to a component which will not cause any significant ocular damage or ocular discomfort at the intended concentration and over the time of intended use.

The invention embraces several embodiments, some of which are outlined below to improve the reader's understanding. One group of embodiments of the invention are ophthalmic compositions which are useful in reducing intraocular pressure, especially intraocular pressure which is associated with glaucoma. The ophthalmic compositions include an amount of a docosanoid active agent selected from the group of docosanoids, analogs thereof, derivatives thereof, metabolites thereof, salts thereof, or combinations thereof, which are effective to treat elevated intraocular pressures. Another group of embodiments are methods of reducing intraocular pressure and treating glaucoma by topical application of the aforementioned ophthalmic compositions. However, a person having ordinary skill in the art may vary some of the elements of the embodiments without departing from the spirit and scope of the invention.

One embodiment of the invention is a composition which has a reduced concentration of strong preservative, and correspondingly, generates less ocular irritation. Unexpectedly, it has been found that the use of certain non-ionic tonicity adjusting agents enhances the preservative effectiveness of strong preservatives in compositions containing docosanoid active agents. This allows for a reduced concentration of strong preservatives in the composition. In addition, chelating agents may be added to further boost preservative efficacy and reduce the required concentration of strong preservative. Thus, one embodiment of the invention is a composition which includes (1) a docosanoid active agent (e.g. isopropyl unoprostone), (2) a strong preservative (e.g., benzalkonium chloride), and (3) a non-ionic tonicity enhancing agent (e.g., a simple sugar such as mannitol) effective in increasing the preservative efficacy relative to a composition including solely a strong preservative.

In particular, the complete eradication of *Psuedomonas Aeriginosa* is desired. While benzalkonium chloride (BAK) kills nearly all Psuedomonas, there may remain some which are resistant to BAK. Over time, the BAK-resistant Psuedomonas may propagate to a concentration which is unacceptable. Thus, it is preferable to include a preservative efficacy enhancer to eliminate BAK-resistant Psuedomonas.

It is preferable that the preservative efficacy enhancer or second preservative be a well tolerated component which acts via a mechanism which differs from BAK. The strong preservative (e.g., BAK) will handle the bulk of the bioburden. The use of the second well tolerated preservative or enhancer insures complete kill of contaminating microbes and yet minimizes ophthalmic irritation as compared to using abnormally high concentrations of BAK.

A preferred class of preservative efficacy enhancers are chelating agents, such as calcium chelating agents. A preferred calcium chelating agent is ethylene diamine tetraacetate (EDTA). EDTA has been shown to assist in the eradication of BAK-resistant Psuedomonas without substantially altering ophthalmic compatibility or docosanoid efficacy. In addition, EDTA offers the advantage of simultaneously acting as a buffer.

Thus, in a preferred embodiment, the composition includes (1) a docosanoid active agent, (2) a strong preservative, and (3) a non-ionic tonicity enhancing agent, (4) a chelating agent (e.g., edetate sodium). These compositions are especially advantageous in that preservative effectiveness is improved relative to a composition containing a strong preservative alone. This allows for a reduction in the required concentration of the strong preservative, and accordingly less ophthalmic irritation.

Another embodiment of the invention is a composition containing a docosanoid active agent which has an advantageously reduced total surfactant concentration. It is generally desirable to minimize the concentration additives to an ophthalmic formulation in order to minimize potential ocular irritation associated with the additives. However, in order to solubilize docosanoid active agents, a surfactant is typically required. It has been unexpectedly discovered that the combination of two or more non-ionic surfactants, as opposed to a single surfactant, can reduce the total concentration of surfactant required to achieve a given level of solubility of the docosanoid active agent. Thus, this embodiment of the invention relates to a composition which includes (1) a docosanoid active agent, (2) a first non-ionic surfactant (e.g., Polysorbate 80), (3) a second non-ionic surfactant (e.g., a BRIJ surfactant) and (4) an ophthalmically acceptable carrier. This embodiment of the invention offers advantages in reduced ocular irritation and reduced raw material (surfactant) requirements.

Yet another embodiment of the invention relates to the difficulties in achieving solubility of docosanoid active agents. In order to solubilize the active agent, a non-ionic surfactant, preferably Polysorbate 80, is added to the formulation. Thus, increasing the docosanoid concentration to the preferred ranges described herein requires a corresponding increase in the surfactant concentration, in order to maintain the docosanoid in solution. However, the Polysorbate 80 surfactant deactivates the commonly used ophthalmic preservative benzalkonium chloride (BAC). Thus, an increase in surfactant reduces the preservative effectiveness. In sum, an increase in therapeutic efficacy which is achieved by increasing active agent concentration results in the need for an increase in Polysorbate 80 concentration and therefore a decrease in preservative effectiveness. Accordingly, improvements in both preservative effectiveness and efficacy of the cited formulations are difficult to achieve.

However, it has been unexpectedly found that the use of non-ionic tonicity adjusting agents appreciably improves the action of the preservative in the presence of surfactant. Thus, in order to minimize the aforementioned preservative deactivation problem, a preferred composition includes (1) a docosanoid active agent, (2) a strong preservative (e.g., BAK), (3) a non-ionic surfactant which increases solubility of the docosanoid active agent but decreases the preservative effectiveness of the strong preservative (e.g., Polysorbate 80), and (4) a preservative enhancer which increases the effectiveness of the strong preservative (e.g., mannitol or EDTA), and (5) an ophthalmically acceptable carrier. Thus, the efficacy and preservative effectiveness may be simultaneously improved in the present formulations, while maintaining a solution form, by optimizing the concentrations of active agent, surfactant, non-ionic tonicity adjusting agent, and preservative.

Some prior art anti-glaucoma pharmaceutical formulations have used salts such as sodium chloride to adjust tonicity to ophthalmically acceptable levels (e.g., about 0.8 to about 1.0 mg/ml NaCl equivalents). However, ionic tonicity adjusting agents have been found by the present inventors to reduce the solubility of the docosanoid active agents. Thus, another advantage of the use of non-ionic tonicity adjusting agents (e.g., mannitol) in the present invention is the increased solubility of salts of the active agent.

In accordance with several preferred inventive embodiments disclosed herein, a preferred composition includes:

(a) about 0.06 to about 0.24 weight percent isopropyl unoprostone;
(b) about 0.3 to about 2 weight percent of two non-ionic surfactant selected from the group consisting of CREMOPHOR RH, BRIJ 97, BRIJ 98, CREMOPHOR EL, Polysorbate 80 and mixtures thereof;
(c) about 0.01 to about 0.20 weight percent benzalkonium chloride;
(d) about 0.01 to about 0.1 weight percent EDTA;
(e) about 0.10 to about 10.0 weight percent mannitol;
(f) about 0.01 to about 0.05 molar of an ophthalmically acceptable buffer;
(g) an ophthalmically acceptable carrier;
in which the pH is adjusted to about 4.5 to about 8.0.

The active agents useful in accordance with the invention may be selected from the group consisting of docosanoids, metabolites thereof, analogs thereof, derivatives thereof, salts thereof, docosanoid prodrugs, and mixtures thereof, referred to herein as "docosanoid active agent" or merely "active agent". Thus, the active agent is not limited by the specific form of the active, i.e., whether in free acid or salt form. Rather, the docosanoid active agent is active in that the agent causes a reduction of intraocular pressure (IOP) when applied to the ocular environment of a patient in need of reduction of intraocular pressure.

A docosanoid, as used herein, refers to a group of compounds related to docosahexaneoic acid. Docosanoids are found in human and animal tissues and organs and may be synthetically produced. The preferred docosanoids are those which are useful in therapeutic ophthalmic applications, especially those which reduce intraocular pressure.

A group of docosanoids which have been found to be useful in decreasing intraocular pressure are disclosed in U.S. Pat. Nos. 4,599,353; 5,296,504; 5,422,368; and 5,578,618. These patents are incorporated herein by reference for the teaching and examples of docosanoid active agents which are useful in reducing intraocular pressure.

A particularly preferred group of active agents are described more fully in U.S. Pat. Nos. 5,106,869; 5,221,763 5,208,256; 5,001,153; 5,151,444; 5,166,178 and 5,212,200, each of which is incorporated herein by reference for the disclosure of compounds useful in the present invention.

Docosanoids of the present invention may be docosanoid salts, or those docosanoids with an esterified carboxyl group. Suitable docosanoid salts are ophthalmically acceptable salts, including without limitation thereto, salts of alkali metals such as sodium or potassium; salts of an alkaline earth metal such as calcium or magnesium; salts of ammonia, methylamine, dimethylamine, cyclopentylamine, benzylamine, piperidine, monoethanolamine, diethanolamine, monomethylmonoethanolamine, tromethamine, lysine and tetralkylammonia; and the like and mixtures thereof Suitable docosanoid esters are ophthalmically acceptable esters, including without limitation thereto, methyl, ethyl, propyl, butyl, isopropyl, t-butyl, 2-ethylhexyl, straight or branched-chain alkyl esters which may contain an unsaturated bond. Suitable esters include an ester having an alicyclic group such as a cyclopropyl, cyclopentyl, olr cyclohexyl group; an ester containing an aromatic group such as a benzyl or phenyl group (wherein the aromatic group may contain one or more substituents); a hydroxyalkyl or alkoxyalkyl ester such as hydroxyethyl, hydroxyisopropyl, polyhydroxyisopropyl, methoxyethyl, ethaoxyethyl or methoxyisopropyl groups; an alkysilyl ester (e.g., a trimethylsilyl or triethylsilyl ester); and a tetrahydropyranyl ester.

Most preferred are docosanoids as disclosed in U.S. Pat. No. 5,208,256, which is incorporated herein by reference for its disclosure of docosanoid compounds. A particularly preferred docosanoid is isopropyl unoprostone. The structure of isopropyl unoprostone is given below and a method of preparation is outlined in U.S. Pat. No. 5,212,200, which is incorporated by reference.

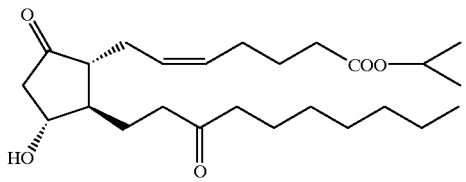

The preferred docosanoid concentration is an amount which will substantially reduce intraocular pressure (IOP) of an eye which has elevated IOP, especially in a patient suffering from glaucoma. Clearly the required concentration depends on a number of factors, including the efficacy of the docosanoid in the presence of the other components, the volumetric amount of medicament applied, and the frequency and duration of application.

It has been determined that concentrations of active agents within the range of about 0.001 to about 0.30 weight percent are more efficacious for reducing intraocular pressure than concentrations above or below this range. In particular, a concentration of about 0.06 to about 0.24 weight percent active agent is preferred, while a concentration of about 0.10 to about 0.20 is more preferred. However, the preferred concentration in any specific application depends on a number of factors, such as the concentrations and chemical nature of other ingredients as well as the delivery method and conditions. Moreover, quite unexpectedly, further increases in active agent concentrations outside these preferred ranges may actually cause less of the desired decrease in intraocular pressure than the concentrations in the preferred ranges.

A surfactant, as used herein, refers to a surface active agent which improves the solubility of a substance, e.g. an active or drug, in a solvent. A non-ionic surfactant, as used herein, refers to a surfactant which possesses no easily ionizable groups.

U.S. Pat. No. 5,208,256 discloses the use of Polysorbate 80 as a surfactant for docosanoid-containing ophthalmic compositions. Polysorbate 80 improves the solubility of isopropyl unoprostone, so that a higher concentration of isopropyl unoprostone can be used in a solution form.

However, it has been discovered that while increasing the Polysorbate 80 concentration allows for increases in the docosanoid concentration in solution, the preservative effectiveness decreases with increasing Polysorbate 80 concentrations. Moreover, it is desired to increase both the efficacy (e.g., by increasing the docosanoid concentration) and preservative effectiveness of the known docosanoid-containing ophthalmic formulations. Thus, it has been determined that use of more Polysorbate 80 has the disadvantage of decreasing preservative effectiveness, while less Polysorbate 80 has the disadvantage of reducing prostaglanin in solution and thereby reducing efficacy.

One embodiment of the present invention offers a solution to these problems by using a combination of two or more non-ionic surfactants. Certain combinations of non-ionic surfactants have been found to increase docosanoid active agent solubility without reducing preservative effectiveness as much as Polysorbate 80 alone in the same concentration.

A preferred group of non-ionic surfactants are those which exhibit better ophthalmic tolerance than Polysorbate 80 alone and/or which do not reduce preservative effectiveness or reduce preservative effectiveness less than Polysorbate 80 alone in the same concentration.

The first and second non-ionic surfactants may be selected from a group of non-ionic surfactants including, without limitation thereto, polyoxyethylene sorbitan fatty acid esters such as Polysorbates 20, 60 and 80; polyoxyethylene alkyl ethers such as Brij's (e.g., BRIJ 97 or BRIJ 98 from ICI Surfactants, Wilmington, Del.), Cremophors (such as Cremophor RH or Cremophor EL), Volpo (e.g., VOLPO 10 and VOLPO 20 from Croda, Inc., Parsippany, N.J.) and equivalents thereof. A preferred group includes polyoxyethylene 20 oleate (e.g., Polysorbate 80), Polyoxyl 10 oleyl ethers (e.g., Brij 97) and Polyoxyl 20 oleyl ethers (e.g., Brij 98).

A particularly preferred combination of surfactants is the combinations of a polyoxyethylene sorbitan fatty acid ester (especially Polysorbate 80) with a polyoxyethylene alkyl ethers (especially BRIJ 97 or BRIJ 98).

Thus, use of at least two surfactants together provides an unexpected synergistic result in that the total concentration of surfactant required to achieve a desired docosanoid active agent solubility is less that the concentration required for an individual surfactant. In addition, certain combinations of surfactants actually improve the preservative effectiveness. Specifically, the combination of Polysorbate 80 with a BRIJ surfactant improves BAC preservative effectiveness relative to the same concentration of Polysorbate 80 alone.

Furthermore, this combination of surfactants improves the emulsion stability of the formulation.

The total concentration of surfactant used depends, in large part, on the solubilizing character of the particular surfactant or surfactants and the concentration and chemical nature of the particular docosanoid active agent which the surfactant is intended to solubilize. In general, the total surfactant concentration may range from about 0.1 to 5 weight percent. A preferred surfactant concentration is about 0.3 to 2.0 weight percent. More preferably, the surfactant concentration is about 0.5 to 1.5 weight percent.

A "preservative", as used herein, refers to an additive which inhibits both microbial growth and kills microorganisms which inadvertently contaminate the ophthalmic solution upon exposure to the surroundings. The preservative may be selected from a variety of well known preservatives, including hydrophobic or non-charged preservatives, anionic preservatives, and cationic preservatives. A "preservative enhancing agent", as used herein, refers to an additive which increases the preservative effectiveness of a preservative, or the preservative effectiveness of a preserved formulation, but which would not typically be used solely to preserve an ophthalmic formulation.

Cationic preservatives include, without limitation thereto, polymyxin B sulfate, quaternary ammonium compounds, poly(quaternary ammonium) compounds, p-hydroxybenzoic acid esters, certain phenols and substituted alcohols, benzalkonium chloride, benzoxonium chloride, cetylpridinium chloride, benzethonium chloride, cetyltrimethyl ammonium bromide, chlorhexidine, poly (hexamethylene biguanide), and mixtures thereof. Poly (quaternary ammonium) compounds include BUSAN 77, ONAMER M, MIRAPOL A15, IONENES A, POLYQUATERNIUM 11, POLYQUATERNIUM 7, BRADOSOL, AND POLYQUAT D-17-1742. A preferred preservative for the ophthalmic field is benzalkonium chloride.

Anionic preservatives include, without limitation thereto, 1-octane sulfonic acid (monosodium salt); 9-octadecenoic acid (sulfonated); ciprofloxacin; dodecyl diphenyloxide-disulfonic acid; ammonium, potassium, or sodium salts of dodecyl benzene sulfonic acid; sodium salts of fatty acids or tall oil; naphthalene sulfonic acid; sodium salts of sulfonated oleic acid; organic mercurials such as thimerosal (sodium ethylmercurithiosalicylate); thimerfonate sodium (sodium p-ethylmercurithiophenylsulfonate).

Hydrophobic or non-ionic preservatives include, without limitation thereto, 2,3-dichloro-1,4-naphthoquinone; 3-methyl-4-chlorophenol (PREVENTOL CMK); 8-hydroxyquinoline and derivatives thereof; benzyl alcohol; bis(hydroxyphenyl) alkanes; bisphenols; chlorobutanol; chloroxylenol; dichlorophen[2,2'-methylene-bis(4-chlorophenol)] (PANACIDE); ortho-alkyl derivatives of para-bromophenol and para-chlorophenol; oxyquinoline; para-alkyl derivatives of ortho-chlorophenol and ortho-bromophenol; pentachlorophenyl laurate (MYSTOX LPL); phenolic derivatives such as 2-phenylphenol, 2-benzyl-4-chlorophenol, 2-cyclopentyl-4-chlorophenol, 4-t-amylphenol, 4-t-butylphenol, and 4- and 6-chloro-2-pentylphenol; phenoxy fatty acid polyester (PREVENTOL B2); phenoxyethanol; and phenylethyl alcohol.

In one embodiment, the preservative is present in the solution in an amount sufficient to kill microbes which may inadvertently enter the dispensing container over the period of use. The desirable concentration will depend on a number of factors, including the strength of the preservative, the conditions of dispenser use, and the length of time the dispenser and solution will be in service. Generally, the strong preservative may be present in a concentration from about 0.00005 to about 0.2 weight percent, more preferably the concentration is about 0.005 to about 0.2 weight percent, and even more preferably, the strong preservative concentration is about 0.01 to about 0.015 weight percent.

An ophthalmically acceptable agent which enhances the effectiveness of the preservative may be advantageously added to the formulation. Examples of preservative enhancing agents useful in accordance with the present invention include, without limitation thereto, chelating agents such as ethylene diamine tetraacetic acid (EDTA), derivatives thereof, salts thereof and mixtures thereof.

The preservative enhancing agent is intended to overcome any remaining microbial burden which the strong preservative did not. For example, while BAK kills nearly all Psuedomonas, there may remain some resistant strain or strains, which may propagate over time. Thus, it is desirable to add a preservative enhancing agent, such as EDTA, to kill the remaining BAC-resistant Psuedomonas. It is believed that EDTA destroys the Psuedomonas by chelation with $Ca^+$ ions. Accordingly, a preferred class of weak preservatives are chelating agents, especially calcium chelating agents.

The use of EDTA is particularly preferred in part because EDTA prevents the growth of BAK-resistant Psuedomonas. However, EDTA has also been found to have advantages in addition to its preservative enhancing function. EDTA can be used to buffer the formulation to achieve the desired pH. Further, EDTA may provide a stabilization function for the docosanoid active agent, thereby inhibiting degradation and increasing shelf life.

The concentration of preservative enhancing agent which is preferred will depend on a number of factors, such as the efficacy of the strong preservative at the chosen concentration and the preservative enhancing effectiveness of the preservative enhancing agent. The concentration of preservative enhancer should be high enough to deactivate amounts of Psuedomonas which are dangerous to the patient, but the concentration should be low enough to avoid any substantial ocular discomfort.

If a chelating agent such as EDTA is used, a concentration of about 0.01 to about 0.1 weight percent is preferred. More preferably, the concentration is about 0.03% to about 0.07%.

Another additive which was determined, quite unexpectedly, to enhance the preservative effectiveness of formulations containing docosanoid active agents is mannitol. It is known to use mannitol to adjust tonicity of an solution to improve ophthalmic compatibility, e.g., by adjusting to nearly an isotonic state. However, the preservative enhancing effect was unexpectedly found in formulations containing docosanoid active agents. In general, it is believed that other non-ionic tonicity adjusting agents, especially other simple sugars, may perform the same function.

Thus, use of one or more preservative enhancers can provide at least two advantages. First, the amount of strong preservative, which may cause irritation to some patients, required for a given level of preservation is reduced. Second, the preservative enhancers may be chosen so that they serve functions in addition to improving preservation of the formulation.

An additional weaker preservative may be added to the container. The weaker preservative, at the concentrations of use, should not be sufficiently potent to cause irritation of the target tissue which the solution will contact. Examples of weaker preservatives useful in accordance with the present invention include, without limitation thereto, peroxides, such as hydrogen peroxide;. peroxide-generating species, such as an alkali perborate or a combination of sodium perborate, boric acid, and sodium borate; urea peroxide; sodium peroxide carbonate; sodium persulfate; sodium perphosphate; and poly(vinyl pyrrolidone) hydrogen peroxide. A preferred weak preservative is a perborate such as sodium perborate.

If a peroxide or peroxide-generating species is used, the peroxide concentration should be less than about 0.1 weight percent, preferably about 0.004 to 0.05 weight percent, more preferably about 0.001 to 0.02 weight percent.

The addition of a buffer offers at least two advantages. First, the buffer helps maintain the pH of the formulation at an ophthalmically acceptable level for instillation directly into the eye. Second, incorporating a buffer early in the manufacturing process reduces the complexity of controlling the pH during manufacturing.

A variety of ophthalmically acceptable buffers may be used. For example, borate buffers such as a combination of boric acid and sodium borate, phosphate buffers, citrates, lactates, equivalents thereof and mixtures thereof.

Also, as mentioned earlier EDTA, which is a preferred weak preservative, may serve a buffering function. Thus, EDTA may advantageously be used to serve at least two functions, i.e., to adjust and maintain the pH and to act as a preservative enhancer. It should be noted that EDTA may further serve as a stabilizer for the active agent, i.e., inhibiting degradation of the active agent (e.g., by chelating metal ions which may catalyze degradation or acting as an antioxidant).

Tonicity adjusting agents may be added to the ophthalmic compositions in order to improve ophthalmic compatibility, i.e., to adjust tonicity to approximate that of the tears. A wide variety of tonicity adjusting agents may be used. Useful ophthalmic tonicity adjusting agents include, without limitation thereto, sodium chloride, mannitol, benzalkonium chloride, phedrine chloride, procaine chloride, chloramphenicol, sodium citrate, mixtures thereof or the like.

However, non-ionic tonicity adjusting agents are preferred in order to maximize the solubility of the non-ionic docosanoid. Examples of useful non-ionic tonicity adjusting agents include mannitol, sorbitol, glycerol, polyethylene glycols (PEG), polypropylene glycols (PPG), sorbitol and mixtures thereof. A preferred non-ionic tonicity adjusting agent is mannitol.

In addition to the unexpected enhancement of preservative effectiveness, certain non-ionic tonicity adjusting agents may serves additional functions in ophthalmic formulations containing docosanoid active agents. For example, it has been unexpectedly discovered that mannitol increases the solubility of isopropyl unoprostone, a preferred active agent. Thus, use of appropriate non-ionic tonicity adjusting agents can (1) result in lower requirements for strong preservatives, which may cause ocular irritation, (2) reduce the concentration of solubility enhancers and/or reduce the amount of active agent required to achieve a chosen active concentration in solution, and (3) adjust the tonicity to ophthalmically acceptable levels.

The tonicity adjusting agent concentration is typically determined by adding sufficient tonicity adjusting agent to produce a formulation with is substantially isotonic, in order to maximize patient comfort. An isotonic solution is one which may be expressed as having a concentration equivalent to about 0.9 mg/ml sodium chloride in deionized water. Substantially isotonic, as used herein, refers to a formulation having about 0.8 to 1.0 mg/ml NaCl equivalents.

In order to achieve a substantially isotonic solution, about 0.1 to 10 weight percent of non-ionic tonicity adjusting agent should be added to the formulation. More preferably, the formulation will include about 1 to 7 weight percent of non-ionic tonicity adjusting agent. Even more preferably, the formulation will include about 3 to 5 weight percent of non-ionic tonicity adjusting agent.

A preferred solvent for the present invention is water, for example, in the form of distilled water or physiological saline. However, the invention is not limited to a particular solvent or diluent, except that the solvent must be ophthalmically compatible under the conditions of intended use. Other examples of diluents for producing a non-aqueous suspension include, without limitation thereto, edible oils, liquid paraffins, mineral oil, propylene glycol, p-octyldodecanol, mixtures thereof and the like.

While the docosanoid formulations described herein are useful in treating ocular hypertension without additional actives, additional actives may be desirable and are within the scope of the invention. For example, the present formulations may include conventional cholinergic ocular hypertensive agents such as pilocarpin or carbachol; anticholinesterases such as demecarium, D.F.P. or echothiophate; miotics such as physostigmine salicylate or pilocarpine hydrochloride; and antiinflammatories such as diclofenac, penicillin, sulfonamide, chloramphenicol, cortisone or chlorpheniramine.

The aforementioned actives are listed to further the reader's understanding of the various embodiments of the invention. Thus, the list of actives, provided above for addition to the present formulations, is not exhaustive and the invention is not so limited.

The present ophthamic compositions may be applied to the ocular tissue or ocular fluids via a number of techniques. For example, a solution or slurry of the ophthalmic composition may be directly instilled into the eye in a droplet, spray or mist form. Alternatively, a drug delivery device with a reservoir (e.g., a polymeric network), which holds the ophthalmic composition, may be inserted into the ocular cavity (e.g., under the eyelid) and left for an extended period of time. The compositions may also be applied transdermally, including by electrotransport, preferably to skin areas near the eye. Injection, either subcutaneous or intraocular, and oral administration may also be useful delivery routes.

However, application of the ophthalmic compositions to the ocular fluids by dropwise addition is currently a preferred method. The number of drops and number of applications per day may vary, depending, inter alia, on the composition efficacy, patient tolerance and relative state of the disease.

Thus, one embodiment of the invention is a method of reducing ocular hypertension, which involves administering to the ocular fluids or ocular tissue an ophthalmic composition including a docosanoid active agent which is selected from the group consisting of docosanoids, metabolites thereof, derivatives thereof, salts thereof, and mixtures thereof; an ophthalmic preservative; a non-ionic toncity adjusting agent; and an ophthalmically acceptable carrier. The non-ionic tonicity adjusting agent is preferably present in a concentration sufficient both to adjust the tonicity of the composition and to increase the preservative effectiveness. The composition is effective in lowering intraocular pressure when administered to a patient in need of a reduction in intraocular pressure.

Another embodiment of the invention is a method of reducing ocular hypertension, which includes administering to the ocular fluids or ocular tissue an ophthalmic composition including a docosanoid active agent; a first non-ionic surfactant; a second non-ionic surfactant; and an ophthalmically acceptable carrier. The total surfactant concentration is lower than the surfactant concentration which would be required to solubilize the docosanoid active agent for either individual non-ionic surfactant.

Yet another embodiment is a method of reducing ocular hypertension, which includes administering to the ocular fluids or ocular tissue an ophthalmic composition including a docosanoid active agent; a strong preservative; a non-ionic surfactant which increases solubility of the docosanoid active agent but decreases the preservative effectiveness of the strong preservative; a preservative enhancer which increases the effectiveness of the strong preservative; and an ophthalmically acceptable carrier.

The previous disclosure will enable one having ordinary skill in the art to practice the invention. In order to better enable the reader to understand specific embodiments and the advantages thereof, reference to the following examples is suggested. However, the invention is not limited to the various embodiments illustrated in the Examples; the Examples are merely provided to enhance the reader's understanding of the invention.

EXAMPLE 1

A 0.12% isopropyl unoprostone ophthalmic formulation was prepared in accordance with the following procedure. A surfactant solution was prepared by dissolving about 0.517 grams of Polysorbate-80 and about 0.221 grams of Brij-97 were dissolved in about 70 grams of distilled water. The surfactant solution was added to about 0.132 grams of isopropyl unoprostone (Ueno Fine Chemicals, Osaka, Japan) and stirred overnight. About 1.034 grams of about 1.06 weight percent benzalkonium chloride (BAC) solution, about 11.0 grams of 0.01 molar phosphate buffer, and about 0.011 grams of ethylenediamine tetraacetate (EDTA) were added to the isopropyl unoprostone solution and mixed until dissolved. Distilled water was added to the resultant solution to bring the weight up to 90% of the final desired weight (110 grams). About 5.153 grams of mannitol was added to the solution, with stirring until dissolved. Finally, distilled water was added to bring the solution to a final weight of 110 grams.

The resultant 0.001 M phosphate solution had a composition, based on weight, of:

0.12% isopropyl unoprostone, 0.47% Polysorbate 80, 0.20% Brij 97, 0.011% BAC, 0.01% EDTA, and 4.7% mannitol.

A clear solution was observed. Accordingly, the surfactants, which had a total weight percentage of 0.67%, completely solubilized the isopropyl unoprostone.

About 30 microliters of the formulation were instilled into the eye of a rabbit at time designated as t=0. The intraocular pressure (IOP) was measured at t=0, 30, 60, 120, 180, 240, 300, and 360 minutes after instillation. IOP was measured by pneumatonometry. IOP, expressed as an average of the samples studied and as a percentage of the t=0 pressure, is shown in TABLE I and graphically in FIG. 1.

EXAMPLE 2

An isopropyl unoprostone ophthalmic formulation was prepared substantially in accordance with the procedure of Example 1, with the exceptions being that formulation included, in weight percentages: 0.18% isopropyl unoprostone, 0.70% Polysorbate 80 and 0.30% Brij 97. Furthermore, no phosphate buffer was necessary, but pH was adjusted with NaOH. The isopropyl unoprostone was completely solubilized as in Example 1.

The IOP lowering effect of this formulation was tested substantially in accordance with the procedure described in Example 1. Intraocular pressure, expressed as a percentage of the t=0 pressure, is shown in TABLE I and graphically in FIG. 1.

EXAMPLE 3

An isopropyl unoprostone ophthalmic formulation was prepared substantially in accordance with the procedure of Example 1, with the exceptions being that formulation included, in weight percentages: 0.24% isopropyl unoprostone, 0.95% Polysorbate 80 and 0.42% Brij 97. The isopropyl unoprostone was completely solubilized as in Example 1.

The IOP lowering effect of this formulation was tested substantially in accordance with the procedure described in Example 1. Intraocular pressure, expressed as a percentage of the t=0 pressure, is shown in TABLE I and graphically in FIG. 1.

TABLE I

| | IOP as a percentage of the initial IOP | | |
|---|---|---|---|
| Time after instillation | Example 1 0.12% isopropyl unoprostone | Example 2 0.18% isopropyl unoprostone | Example 3 0.24% isopropyl unoprostone |
| 0 | 100 | 100 | 100 |
| 30 | 105 | 110 | 111 |
| 60 | 99 | 99 | 110 |
| 120 | 88 | 67 | 82 |
| 180 | 93 | 56 | 80 |
| 240 | 108 | 67 | 84 |
| 300 | 109 | 79 | 83 |
| 360 | 110 | 86 | 92 |

Examination of the data generated from Examples 1–3 shows that a 0.18% isopropyl unoprostone is more effective than 0.12% or a 0.24% isopropyl unoprostone formulations. Accordingly, a preferred range of isopropyl unoprostone concentrations is about 0.12% to about 0.24%.

EXAMPLE 4

An isopropyl unoprostone ophthalmic formulation was prepared substantially in accordance with the procedure of Example 1, with modifications of the relative concentration of the components. The resultant 0.001 M phosphate formulation comprised, in weight percentages:

0.12% isopropyl unoprostone, 0.47% Polysorbate 80, 0.20% Brij 97, 0.010% BAC, 0.01% EDTA, and 4.4% mannitol.

Thus, the total surfactant concentration was 0.67%. The isopropyl unoprostone was completely solubilized as in Example 1. Comparative results are presented in Table II.

EXAMPLE 5

An isopropyl unoprostone ophthalmic formulation was prepared substantially in accordance with the procedure of Example 2, with modifications of the relative concentration of the components, including a substitution of Volpo 10 for Brij 97. The resultant formulation in weight percentages was:

0.12% isopropyl unoprostone,
0.47% Polysorbate 80,
0.20% Volpo 10,
0.013% BAC,
0.05% EDTA, and
4.3% mannitol.

Thus, the total surfactant concentration was 0.67%. The isopropyl unoprostone was completely solubilized as in Example 1. Comparative results are presented in Table II.

EXAMPLE 6

A 0.12% isopropyl unoprostone ophthalmic formulation was prepared in accordance with the following procedure. About 6 grams of sodium chloride and about 0.2 grams of benzalkonium chloride were dissolved in about a liter of distilled water. About 0.12 grams of isopropyl unoprostone and about one (1) gram of Polysorbate 80 were mixed into the BAC solution. The resultant formulation in weight percentages included:

0.12% isopropyl unoprostone,
1.0% Polysorbate 80,
0.020% BAC,
0.6% sodium chloride Thus, the total surfactant concentration was 1.0%. The isopropyl unoprostone was solubilized, i.e., the solution appeared clear. Comparative results are presented in Table II.

EXAMPLE 7

A 0.12% isopropyl unoprostone ophthalmic formulation was prepared substantially in accordance with Example 6, with the exception being that a reduced amount of Polysorbate 80 was used. The resultant formulation included:

0.12% isopropyl unoprostone,
0.85% Polysorbate 80,
0.020% BAC,
0.6% sodium chloride Thus, the total surfactant concentration was 0.85%. The isopropyl unoprostone was solubilized, i.e., the solution appeared clear. Comparative results are presented in Table II.

EXAMPLE 8

A 0.12% isopropyl unoprostone ophthalmic formulation was prepared substantially in accordance with Example 7, with the exception being that a reduced amount of Polysorbate 80 was used. The resultant formulation included:

0.12% isopropyl unoprostone,
0.80% Polysorbate 80,
0.020% BAC,
0.6% sodium chloride Thus, the total surfactant concentration was 0.80%. The isopropyl unoprostone was not completely solubilized, i.e., the solution appeared cloudy. Comparative results are presented in Table II.

The isopropyl unoprostone was not completely solubilized, i.e., phase separation was observed. Comparative results are presented in Table II.

TABLE II

|  | Example 1 | Example 4 | Example 5 | Example 6 | Example 7 | Example 8 |
|---|---|---|---|---|---|---|
| % isopropyl unoprostone | 0.12 | 0.12 | 0.12 | 0.12 | 0.12 | 0.12 |
| % Polysorbate 80 | 0.47 | 0.47 | 0.47 | 1.0 | 0.85 | 0.80 |
| % Brij 97 | 0.20 | 0.20 | — | — | — | — |
| % Volpo 10 | — | — | 0.20 | — | — | — |
| Total % surfactant | 0.67 | 0.67 | 0.67 | 1.0 | 0.85 | 0.80 |
| Solubility | complete | complete | complete | complete | complete | incomplete-cloudy formulation |

Examples 1 and 4–8, along with Table II, show that the combination of Polysorbate 80 with Brij 97 or Volpo 10 solubilizes isopropyl unoprostone better than Polysorbate 80 alone. In Example 8, a 0.80% total surfactant formulation with Polysorbate 80 alone did not adequately solubilize the active, while a 0.67% total surfactant formulation with the combination of surfactants provided complete solubility. Thus, a lower total surfactant concentration may be achieved by using two or more surfactants rather than one surfactant in a formuation containing docosanoid active agents.

EXAMPLE 9

About a 100 gram ophthlamic formulation including 0.12% isopropyl unoprostone was prepared in accordance with the following procedure. About 0.12 grams isopropyl unoprostone and about 1.0 grams Polysorbate 80 were added to a beaker, followed by about 90 grams distilled water. The mixture was stirred until dissolved. About 1.2 grams of an about 1% BAC solution and about 0.05 grams EDTA were added to the resultant solution. About 3.3 grams of mannitol was added with mixing until dissolution was achieved.

The resultant formulation contained:

0.12% isopropyl unoprostone
1.0% Polysorbate 80
0.012% BAC
0.05% EDTA
3.3% mannitol The formulation was subject to standard U.S. Pharmacopia and European Pharmacopia Criteria "A" and "B" preservative effectiveness testing. The formulation passed all three tests. Results are summarized in Table III.

EXAMPLE 10

A formulation was prepared substantially in accordance with the procedure described in Example 9, except that sodium chloride was used as the tonicity adjusting agent instead of mannitol. The formulation had the following composition:

0.12% isopropyl unoprostone
1.0% Polysorbate 80
0.012% BAC
0.05% EDTA
0.6% sodium chloride The formulation failed the European Pharmacopia Criteria "A" and "B" preservative effectiveness tests, while passing the USP test. Results are summarized in Table III.

EXAMPLE 11

A formulation was prepared substantially in accordance with the procedure described in Example 9, except that sodium chloride was used as the tonicity adjusting agent instead of mannitol and additional BAC and EDTA were used. The formulation had the following composition:

0.12% isopropyl unoprostone
1.0% Polysorbate 80
0.013% BAC
0.10% EDTA
0.6% sodium chloride The formulation failed the European Pharmacopia Criteria "A" and "B" preservative effectiveness tests, while passing the USP test. Results are summarized in Table III.

EXAMPLE 12

A formulation was prepared substantially in accordance with the procedure described in Example 9, except that additional BAC and EDTA were used as compared with Example 9. The formulation had the following composition:

0.12% isopropyl unoprostone
1.0% Polysorbate 80
0.013% BAC
0.10% EDTA
3.3% mannitol The formulation passed the European Pharmacopia Criteria "A" and "B" tests as well as the USP test. Results are summarized in Table III.

EXAMPLE 13

A formulation was prepared substantially in accordance with the procedure described in Example 12, except that sodium chloride was substituted for mannitol and additional BAC was used as compared with Example 12. The formulation had the following composition:

0.12% isopropyl unoprostone
1.0% Polysorbate 80
0.014% BAC
0.10% EDTA
0.6% sodium chloride The formulation failed the European Pharmacopia Criteria "A" and "B" preservative effectiveness tests, while passing the USP test. Results are summarized in Table III.

EXAMPLE 14

A formulation was prepared substantially in accordance with the procedure described in Example 13, except that additional BAC was used as compared with Example 13. The formulation had the following composition:

0. 12% isopropyl unoprostone
1.0% Polysorbate 80
0.015% BAC
0. 10% EDTA
0.6% sodium chloride The formulation failed the European Pharmacopia Criteria "A" and "B" preservative effectiveness tests, while passing the USP test. Results are summarized in Table III.

TABLE III

|  | Example 9 | Example 10 | Example 11 | Example 12 | Example 13 | Example 14 |
| --- | --- | --- | --- | --- | --- | --- |
| % isopropyl unoprostone | 0.12 | 0.12 | 0.12 | 0.12 | 0.12 | 0.12 |
| % Polysorbate 80 | 1.0 | 1.0 | 1.0 | 1.0 | 1.0 | 1.0 |
| % BAC | 0.012 | 0.012 | 0.013 | 0.013 | 0.014 | 0.015 |
| % EDTA | 0.05 | 0.05 | 0.10 | 0.10 | 0.10 | 0.10 |
| % mannitol | 3.3 | — | — | 3.3 | — | — |
| % sodium chloride | — | 0.6 | 0.6 | — | 0.6 | 0.6 |
| European Pharmacopia Criteria "A" Microbial Test | PASS | fail | fail | PASS | fail | fail |
| European Pharmacopia Criteria "B" Microbial Test | PASS | fail | fail | PASS | fail | fail |
| U.S. Pharmaecopia Microbial Test | PASS | PASS | PASS | PASS | PASS | PASS |

Examples 9–14 and Table III illustrate that the non-ionic tonicity adjusting agent mannitol enhances preservative effectiveness as compared to the ionic tonicity adjusting agent sodium chloride.

The invention has been described in detail, with reference to certain preferred embodiments, in order to enable the reader to practice the invention without undue experimentation. However, a person having ordinary skill in the art will readily recognize that many of the components and parameters may be varied or modified to a certain extent without departing from the scope and spirit of the invention. Furthermore, titles, headings, definitions or the like are provided to enhance the reader's comprehension of this document, and should not be read as limiting the scope of the present invention. Accordingly, the intellectual property rights to this invention are defined only by the following claims and reasonable extensions and equivalents thereof.

That which is claimed is:

1. A composition comprising:
   (1) a docosanoid active agent;
   (2) a first non-ionic surfactant; and
   (3) a second non-ionic surfactant; and
   (4) an ophthalmically acceptable carrier,
wherein the total surfactant concentration is lower than the surfactant concentration which would be required to solubilize the docosanoid active agent for either individual non-ionic surfactant.

2. A composition of claim 1, wherein said non-ionic surfactants are selected from the group consisting of selected from the group consisting of polyoxyethylene sorbitan fatty acid esters, polyoxyethylene alkyl ethers, and mixtures thereof.

3. A composition of claim 2, wherein said first non-ionic surfactant is a polyoxyethylene sorbitan fatty acid ester and said second non-ionic surfactant is a polyoxyethylene alkyl ether.

4. A composition of claim 3, wherein said first non-ionic surfactant is a Polysorbate compound and said second non-ionic surfactant is Brij compound.

5. A composition of claim 4, wherein the total non-ionic surfactant concentration in the composition is about 0.3 to 2.0 weight percent.

6. A method of reducing ocular hypertension, which comprises administering to the ocular fluids or ocular tissue an ophthalmic composition comprising:
   (1) a docosanoid active agent;
   (2) a first non-ionic surfactant; and
   (3) a second non-ionic surfactant; and
   (4) an ophthalmically acceptable carrier,
wherein the total surfactant concentration is lower than the surfactant concentration which would be required to solubilize the docosanoid active agent for either individual non-ionic surfactant.

7. A method for increasing the effectiveness of a strong preservative in a solution comprising a docosanoid active agent and a non-ionic surfactant, comprising admixing:
   (1) a docosanoid active agent;
   (2) a strong preservative;
   (3) a non-ionic surfactant which increases solubility of the docosanoid active agent but decreases the preservative effectiveness of the strong preservative;
   (4) mannitol in an amount sufficient to increase the effectiveness of the strong preservative; and
   (5) an ophthalmically acceptable carrier.

8. The method of claim 7, wherein said docosanoid active agent is isopropyl unoprostone, said strong preservative is benzalkonium chloride, and said non-ionic surfactant is polysorbate 80.

9. The method of claim 7, further comprising admixing ethylene diamine tetraacetic acid.

* * * * *